(12) United States Patent
McKinnis et al.

(10) Patent No.: US 9,492,638 B2
(45) Date of Patent: Nov. 15, 2016

(54) IMPLEMENTS FOR IDENTIFYING SHEATH MIGRATION

(71) Applicant: Muffin Incorporated, West Lafayette, IN (US)

(72) Inventors: Peter S. McKinnis, West Lafayette, IN (US); Neal E. Fearnot, West Lafayette, IN (US); Kasper Klausen, Helsinge (DK)

(73) Assignee: Muffin Incorporated, West Lafayette, IN (US)

( * ) Notice: Subject to any disclaimer, the term of this patent is extended or adjusted under 35 U.S.C. 154(b) by 286 days.

(21) Appl. No.: 14/068,737

(22) Filed: Oct. 31, 2013

(65) Prior Publication Data

US 2014/0121643 A1    May 1, 2014

Related U.S. Application Data

(60) Provisional application No. 61/721,040, filed on Nov. 1, 2012.

(51) Int. Cl.
*A61M 25/02*    (2006.01)
*A61M 25/01*    (2006.01)
(Continued)

(52) U.S. Cl.
CPC ........ *A61M 25/0105* (2013.01); *A61B 8/0841* (2013.01); *A61B 8/12* (2013.01);
(Continued)

(58) Field of Classification Search
CPC .... A61B 5/06; A61M 2/1418; A61M 25/02; A61M 39/284; A61M 2005/1416; A61M 2025/024

USPC .......................... 600/424; 604/174, 177, 533
See application file for complete search history.

(56) References Cited

U.S. PATENT DOCUMENTS 3,146,778 A    9/1964 Krawiec
4,473,369 A *  9/1984 Lueders ............. A61M 39/1011
                                                  285/419
(Continued)

FOREIGN PATENT DOCUMENTS

DE    20 2010 004 107 U1    6/2010
EP         1 416 443 A1     5/2004
(Continued)

OTHER PUBLICATIONS

English Abstract of DE202010004107.
(Continued)

*Primary Examiner* — Gerald Landry, II
(74) *Attorney, Agent, or Firm* — Woodard, Emhardt, Moriarty, McNett & Henry LLP

(57) ABSTRACT

Attachable implements, systems, and methods for identifying the migration of a medical device extending through a percutaneous insertion site of a patient's skin are disclosed. In one embodiment, an attachable implement for identifying migration comprises a attachable implement body having a coupling surface and a skin contacting surface, the coupling surface arranged to couple to a surface of the medical device, and the skin contacting surface arranged to contact the skin of the patient; wherein the attachable implement body is arranged to be side mountable on the medical device and wherein the attachable implement is configured to move from a first position adjacent to the patient's skin to a second position remote from the patient's skin. Systems, methods, and other embodiments are disclosed.

17 Claims, 11 Drawing Sheets

(51) Int. Cl.
*A61F 2/01* (2006.01)
*A61B 8/12* (2006.01)
*A61B 8/08* (2006.01)
*A61M 25/00* (2006.01)
*A61B 6/12* (2006.01)

(52) U.S. Cl.
CPC ...... *A61F 2/01* (2013.01); *A61B 6/12* (2013.01); *A61B 2050/314* (2016.02); *A61F 2002/011* (2013.01); *A61M 2025/0008* (2013.01)

(56) References Cited

U.S. PATENT DOCUMENTS

| | | | |
|---|---|---|---|
| 4,897,082 A | | 1/1990 | Erskine |
| 4,951,686 A | | 8/1990 | Herlitze |
| 5,114,401 A | | 5/1992 | Stuart et al. |
| 5,226,892 A | | 7/1993 | Boswell |
| 5,239,982 A | | 8/1993 | Trauthen |
| 5,425,367 A | | 6/1995 | Shapiro et al. |
| 6,029,668 A | * | 2/2000 | Freed ............... A61M 16/0488 128/200.26 |
| 6,038,488 A | * | 3/2000 | Barnes .................. G09B 23/28 128/920 |
| 6,080,178 A | | 6/2000 | Meglin |
| 6,156,016 A | * | 12/2000 | Maginot ........... A61M 25/0028 604/264 |
| 6,361,523 B1 | * | 3/2002 | Bierman ............... A61M 25/02 128/DIG. 26 |
| 6,440,077 B1 | | 8/2002 | Jung et al. |
| 6,460,231 B2 | | 10/2002 | Bourgerie |
| 6,551,285 B1 | * | 4/2003 | Bierman ............... A61M 25/02 128/DIG. 15 |
| 6,640,231 B1 | * | 10/2003 | Andersen ............ G06F 17/3061 |
| 6,689,104 B2 | | 2/2004 | Bierman |
| 7,799,015 B2 | * | 9/2010 | Schweikert ........ A61M 39/1011 24/522 |
| 7,914,518 B2 | * | 3/2011 | Raulerson ........... A61M 5/1418 604/250 |
| 2002/0143362 A1 | | 10/2002 | Macoviak et al. |
| 2004/0162544 A1 | * | 8/2004 | Raulerson ........... A61M 5/1418 604/533 |
| 2005/0277909 A1 | * | 12/2005 | McDaniel ......... A61M 25/0097 604/523 |
| 2006/0058738 A1 | * | 3/2006 | Ponzi .................. A61M 25/02 604/180 |
| 2006/0069405 A1 | | 3/2006 | Schaeffer et al. |
| 2006/0129180 A1 | | 6/2006 | Tsugita et al. |
| 2006/0212107 A1 | | 9/2006 | Case et al. |
| 2006/0259137 A1 | | 11/2006 | Artof et al. |
| 2007/0016167 A1 | * | 1/2007 | Smith ............... A61M 25/0009 604/533 |
| 2007/0265564 A1 | | 11/2007 | Daly et al. |
| 2008/0021552 A1 | | 1/2008 | Gabbay |
| 2008/0208129 A1 | | 8/2008 | Carter et al. |
| 2008/0287908 A1 | | 11/2008 | Muni et al. |
| 2009/0018638 A1 | | 1/2009 | Shirley et al. |
| 2009/0143740 A1 | | 6/2009 | Bierman et al. |
| 2009/0149938 A1 | | 6/2009 | Grewe et al. |
| 2009/0254040 A1 | * | 10/2009 | Bierman ............... A61M 25/02 604/180 |
| 2009/0264826 A1 | | 10/2009 | Thompson |
| 2009/0306603 A1 | * | 12/2009 | Bierman ............... A61M 25/02 604/180 |
| 2010/0069880 A1 | * | 3/2010 | Grayzel ............... A61M 25/09 604/509 |
| 2010/0268265 A1 | | 10/2010 | Krolik et al. |
| 2013/0079809 A1 | * | 3/2013 | Hendriksen ........... A61M 25/02 606/200 |

FOREIGN PATENT DOCUMENTS

| | | |
|---|---|---|
| JP | 2007-522907 A | 8/2007 |
| JP | 2008-513147 A | 5/2008 |
| WO | WO 99/16382 | 4/1999 |
| WO | 00/42926 | 7/2000 |
| WO | 03/073961 A1 | 9/2003 |
| WO | 03/090834 A2 | 11/2003 |
| WO | WO 2004/084737 A | 10/2004 |
| WO | WO 2005/102211 A1 | 11/2005 |
| WO | WO 2006/034233 A1 | 3/2006 |
| WO | WO 2006/043276 A2 | 4/2006 |
| WO | WO 2007/143602 | 12/2007 |
| WO | 2009/044316 A1 | 4/2009 |
| WO | 2009/076482 A1 | 6/2009 |
| WO | WO 2012/003369 A3 | 1/2012 |

OTHER PUBLICATIONS

English Abstract of JP2007-522907A.
English Abstract of JP2008-513147A.

* cited by examiner

IMPLEMENTS FOR IDENTIFYING SHEATH MIGRATION

CROSS-REFERENCE TO RELATED APPLICATIONS

This application claims the benefit of U.S. Provisional Application No. 61/721,040, filed Nov. 1, 2012, which is hereby incorporated by reference in its entirety.

FIELD OF THE INVENTION

The present invention pertains generally to systems, implements, and methods for the introduction of medical devices into the body of a patient. In certain aspects, the invention relates to attachable implements useful for the percutaneous introduction of vascular devices, such as vascular filters under ultrasound guidance.

BACKGROUND

Vascular devices are commonly percutaneously introduced under fluoroscopic guidance. For example, vena cava filters are most often placed under fluoroscopic guidance with the injection of contrast agent to provide a cavogram characterizing the site of intended implantation. Such fluoroscopic procedures must be performed in a specially equipped room such as an X-ray suite. This not only necessitates transport of an often critically ill patient to the suite but also adds significant expense to the procedure.

Ultrasound imaging technology, including intravenous ultrasound (IVUS) imaging, has been used to some extent in the diagnosis and in the treatment of patients. However, the images generated with IVUS and other ultrasound technology are often more difficult to interpret for purposes of implant guidance, particularly for physicians or other health care providers who are more accustomed to fluoroscopic images.

Needs exist for improved and/or alternative methods, systems and implements whereby the introduction of vascular devices such as vena cava filters can be guided under ultrasound imaging techniques. In certain of its aspects, the present invention is addressed to these needs.

SUMMARY

In certain aspects, the present disclosure provides attachable implements, systems, and methods for identifying the migration of a medical device, in particular access devices. In accordance with some forms of the invention, such attachable implements are configured to move from a first position where the attachable implement is proximal to the surface of the skin of the patient to a second position where the attachable implement is remote from the surface of the skin. In some embodiments, the present disclosure provides an attachable implement for identifying migration of a medical device that extends through the skin of a patient, comprising: a attachable implement body comprising a coupling surface and a skin contacting surface; the coupling surface arranged to couple to a surface of the medical device; and the skin contacting surface arranged to contact the skin of the patient; wherein the attachable implement body is arranged to be side mountable onto the medical device; and wherein the attachable implement body is configured to move with the medical device from a first position where the skin contacting surface is adjacent to the patient's skin to a second position where the skin contacting surface is remote from the patient's skin, such that an operator may identify that the medical device has migrated. In some instances, the attachable implement body comprises cooperating first and second portions. Additionally, in some embodiments, the first and second portions are pivotably coupled to one another, and, in some embodiments, the first and second portions define a recess that is arranged to receive a portion of the medical device.

The present disclosure also teaches an attachable implement for identifying migration of a medical device that extends through the skin of a patient, comprising: a attachable implement body comprising a coupling surface, a skin contacting surface, and an adherent material; the coupling surface arranged to mate with a surface of the medical device; the skin contacting surface arranged to contact the skin of the patient; and the adherent material positioned on the coupling surface and arranged to adhere the coupling surface to the surface of the medical device; wherein the attachable implement body is configured to move with the medical device from a first position where the skin contacting surface is adjacent to the patient's skin to a second position where the skin contacting surface is remote from the patient's skin, such that an operator may identify that the medical device has migrated. In some embodiments, the attachable implement further comprises a removable film positioned over the adherent material and arranged to protect the adherent material prior to attachment to the medical device. The attachable implement may comprise cooperating first and second portions, and, in some instances, the first and second portions are pivotably coupled to one another. The first and second portions may also define a recess arranged to receive a portion of the medical device.

The present disclosure also describes an attachable implement for identifying migration of a medical device that extends through the skin of a patient, comprising: a attachable implement body comprising a coupling surface, an adherent material, and a skin contacting surface; the coupling surface arranged to mate with a surface of the medical device; the skin contacting surface arranged to contact the skin of the patient; and the adherent material positioned on the coupling surface and arranged to adhere the coupling surface to the surface of the medical device; wherein the attachable implement body is arranged to be side mountable onto the medical device; and wherein the attachable implement body is configured to move with the medical device from a first position where the skin contacting surface is adjacent to the patient's skin to a second position where the skin contacting surface is remote from the patient's skin, such that an operator may identify that the medical device has migrated. In some embodiments, a removable film positioned over the adherent material and arranged to protect the adherent material prior to attachment to the medical device. Additionally, or alternatively, some embodiments comprise cooperating first and second portions defining a recess that is arranged to receive a portion of the medical device. Further forms, objects, features, aspects, benefits, advantages, and embodiments of the present invention will become apparent from a detailed description and drawings provided herewith.

DESCRIPTION OF THE ILLUSTRATED EMBODIMENTS

Figure 1:
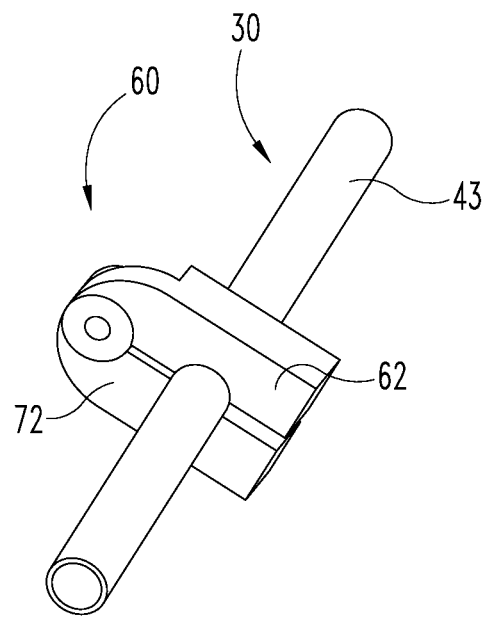
FIG. 1 is a perspective view of one embodiment of the present disclosure.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Typically prior to deployment of an implantable vascular device such as a vena cava filter, a medical professional confirms the positioning of the vascular device and/or a delivery system. With vascular devices percutaneously introduced under fluoroscopic guidance, the medical professional often injects a contrast agent comprising a radiopaque material through the delivery system and into the patient's vasculature so as to confirm positioning of the vascular device and/or the delivery system. In many instances, the contrast agent is dispersed throughout the vessel in which it is injected, either by the pressure and velocity of the agent being injected and/or by the fluid flow within the vessel, e.g., blood. As the contrast agent disperses throughout the vessel, the medical professional is able to observe the area beyond the immediate site of intended implantation to confirm the anatomical positioning of the vascular device and/or the delivery system. However, in procedures using localized imaging systems, such as intravenous ultrasound (IVUS) imaging, this approach may not be available.

Localized imaging technology, including intravenous ultrasound (IVUS), is often inserted into the vessel through a sheath and images an area proximate to the imaging device. Because of space constraints within the sheath and the vessel, the localized imaging device often must necessarily be removed from the sheath and the vascular device prior to insertion of the vascular device and/or delivery system. Once the localized imaging device is removed from the vessel and sheath, the vascular device and/or delivery system may be inserted into the sheath and advanced towards the target delivery site. Unfortunately, since the localized imaging device is removed, the medical professional may be unable to confirm the positioning of the vascular device and/or delivery system prior to deployment which may result in misplacement of the vascular device, leading to an increased risk of device failure and/or device migration.

It was discovered that, in some instances, misplacement of the vascular device was due to the vascular device and/or delivery system not being sufficiently advanced through the sheath. This resulted in the vascular device being deployed partially or entirely within the sheath and not within the vessel as desired. To solve this problem, it was decided, in some instances, to index the delivery system to the sheath prior to deployment of the vascular device so as to ensure that the vascular device would not be deployed within the sheath.

Unfortunately, in some cases, it was found that the vascular device was still misplaced within the vessel of the patient, often being positioned too far distally or too far proximally of the target delivery site. It was determined that while the medical professional may remove the vascular device and/or delivery system to re-advance the imaging device through the sheath in the vessel so as to reference an anatomical landmark, such as a branch vessel, this would be time consuming and may still not prevent the subsequent misplacement of an implantable vascular device after withdrawal of the imaging device and advancement of the vascular device and/or delivery system through the sheath and the vessel. Therefore, additional improvements were desired.

It was discovered that by positioning an external marker on the sheath and indexing that marker to the body of the patient, a medical professional may maintain the position of the sheath with respect to the patient, more specifically the target delivery site in the patient, and accurately and precisely deploy the vascular device at the desired location within the patient's vasculature. In some instances, the medical professional may contact the external marker to the skin of the patient and/or retain the marker a predetermined distance from the patient's skin during deployment of the vascular device. Similarly, in some instances, a medical professional may simply observe the positioning of the marker with respect to a portion of the body of the patient at the time of IVUS imaging and prior to the time of deployment of the vascular device to determine whether the sheath has moved.

Accordingly, the disclosed embodiments and variations thereof may be used to mark the depth that an access device, such as a catheter and/or a sheath, extends into the body of a patient. In some instances, the external marker may be used for a diagnostic technique. For instance, the external marker may be used for the in-vitro determination of the positioning of a distal portion of a sheath. Additionally, the disclosed embodiments may be used to determine whether the access device has migrated from a target location within the body of the patient and/or resist a migratory movement of the access device in one or more directions.

For simplicity, some of the following embodiments will be discussed with reference to the positioning of an attachable implement for identifying the migration of a sheath that extends through the skin of a patient and into the patient's inferior vena cava. However, it is not intended that the present disclosure be limited to such. It is contemplated that the disclosed embodiments and variations thereof may be used to identify the migration of other access devices accessing other locations within the body of a patient.

Figure 2:
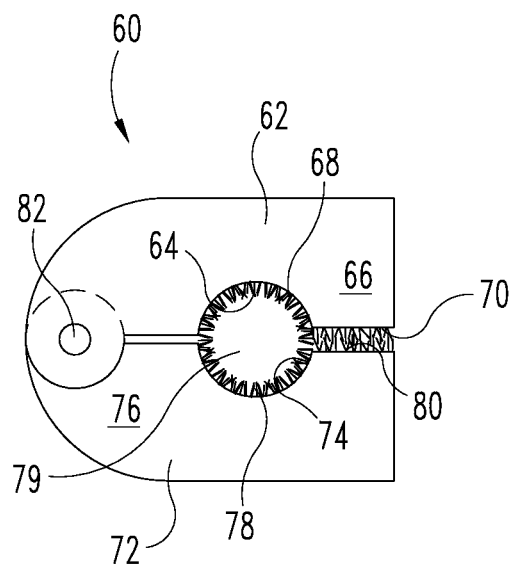
FIG. 2 is a front side view of the embodiment illustrated in FIG. 1 in a closed configuration.
Figure 3:
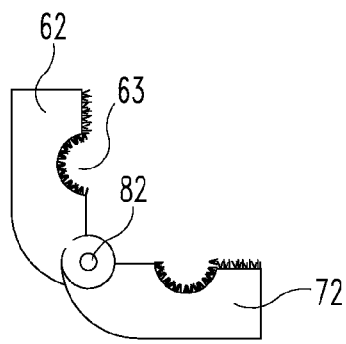
FIG. 3 is a front side view of the embodiment illustrated in FIG. 1 in an open configuration.
Figure 4:
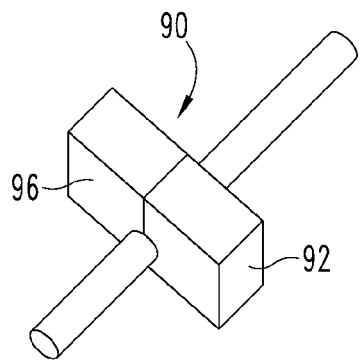
FIG. 4 is a perspective view of one embodiment of the present disclosure.
Figure 5:
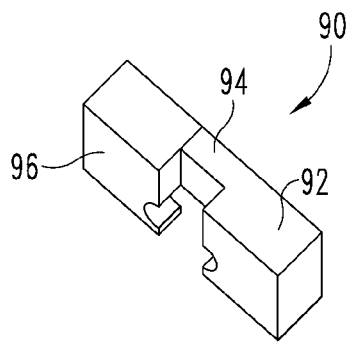
FIG. 5 is a perspective view of the embodiment illustrated in FIG. 4 in an open configuration.
Figure 6:
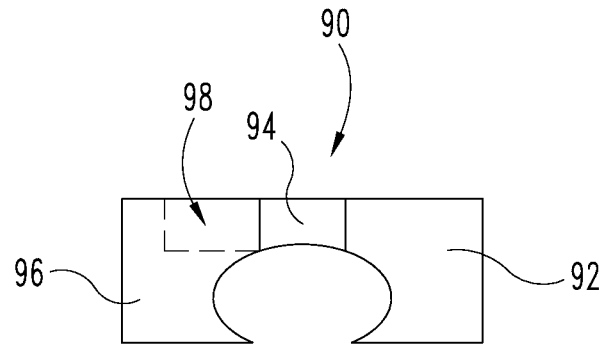
FIG. 6 is a front side view of the embodiment illustrated in FIG. 4 in an open configuration.
Figure 7:
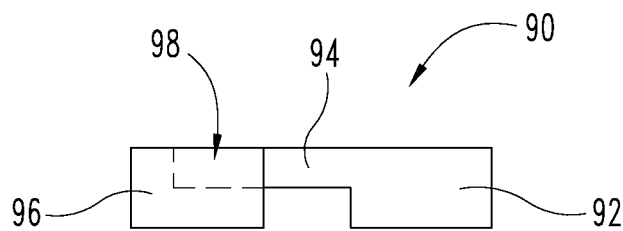
FIG. 7 is a top view of the embodiment illustrated in FIG. 4 in an open configuration.

FIGS. 1-3 illustrate an attachable implement, such as a clip, that is useful for identifying the migration of a medical device that extends through the skin of a patient. The attachable implement 60 can comprise an attachable implement body having a first portion 62 and a second potion 72. In several embodiments, one or more regions of the first portion 62 and/or second portion 72 are arranged to couple the first portion 62 and/or the second portion 72 to the access device 30. For example, the first portion 62 may be arranged to define a recess 63 that matches and/or constrains a section of the access device 30. In some instances, the first portion 62 of the attachable implement 60 may comprise a coupling surface 64 arranged to couple to the outer surface of an access device 30 and a skin contacting surface 66 arranged to contact the surface of the skin of a patient and provide a reference for when the attachable implement 60 has moved away from a position proximal to the patient's skin.

Coupling surface 64 is arranged to resist longitudinal movement of the attachable implement 60 or a portion thereof, such as the first portion 62, along the outer surface of the access device 30. In some instances, coupling surface 64 may also resist the rotational movement of the attachable implement 60, or a portion thereof, around the outer surface of the access device 30. In some embodiments, coupling surface 64 is arranged to mate with an outer surface of an access device 30. For example, coupling surface 64 may define the recess 63 that matches and/or constrains the outer surface of the access device 30. Similarly, in some instances, coupling surface 64 is arranged so as to substantially conform to the outer perimeter of the access device 30.

In several embodiments, the coupling surface 64 of the attachable implement 60 comprises a resisting member 68 that increases the resistance to movement of the coupling surface 64 relative to the outer surface of the access device 30. In some embodiments, the resisting member can fasten the first portion 62 of the attachable implement 60 to the surface of the access device 30 and/or can increase the frictional resistance to movement of the first portion 62 of the attachable implement 60 along a length of the access device 30. For example, the resisting member 68 may comprise an adherent material, such as an adhesive member and or an elastomeric rubber to name a few non-limiting examples, that adheres the coupling surface 64 to a surface of the access device 30. Suitable adherent materials include adhesives and rubbers apparent to those of ordinary skill in the art and can include biocompatible and bioabsorable materials. Additionally, as will be discussed in more detail later, the resisting member 68 can be positioned on various surfaces, including more than one surface, of the attachable implement 60. In some embodiments, the resisting member 68 is covered with a removable member, such as a protective film, that is removed prior to joining the coupling surface 64 with the surface of the access device 30, such as adhering the coupling surface 64 to the surface of the access device 30.

In some instances, the first portion 62 also comprises a surface 70 that faces a second portion 72 of the attachable implement 60. In some instances, the surface 70 may be arranged so as to lock the first portion 62 to the second portion 72. For example, an adhesive may be positioned on the surface 70 of the first portion to adhere the first portion 62 to surface 80 of the second portion 72.

The second portion 72 of the attachable implement 60, in some instances, is arranged similar to the first portion 62. For example, the second portion 72 may also comprise a coupling surface 74 arranged to couple to a surface of an access device so as to resist the longitudinal movement of the second portion 72 along the access device 30. Additionally, the second portion 72 may comprise a skin contacting surface 76 that may be arranged to contact the surface of a patient's skin and be moved to a position remote from the surface of the patient's skin so as to provide an indication that the access device has migrated from a desired location. In some embodiments, the second portion 72 comprises a resisting member 78 similar to the resisting member 68 of the first portion. The resisting member 78 of the second portion being positioned on the coupling surface 74 and/or a surface 80 so as to resist the movement of the access device 30 along the coupling surface 74 and/or so as to couple the second portion 72 to the first portion 62 of the attachable implement 60. Similarly, the resisting member 78 may be covered with a removable member, such as a protective film.

In many embodiments, the first portion 62 and the second portion 72 are coupled such that the first portion 62 and/or second portion 72 maybe configurable between a first configuration and a second configuration. For example, the first portion 62 may be pivotably coupled to the second portion 72. In some instances, the first configuration resembles an open configuration, such as when a pivotably coupled first portion 62 and second portion 72 are rotated away from one another, leaving an opening for an access device 30 to be positioned between regions of the first portion 62 and the second portion 72 (FIG. 3). In some instances, the attachable implement 60 is arranged to be side mountable onto an access device 30. For example, the first portion 62 and second portion 72 of the attachable implement 60 may be arranged such that they are coupleable to an access device 30 from a direction transverse to the longitudinal axis of a portion of the access device 30.

The second configuration can be a closed configuration, and, in some instances, defines a recess. For example, the coupling surface 64 of the first portion 62 and the coupling surface 74 of the second portion 72 may cooperate to define a recess 79. In some instances, the recess 79 matches the shape of the access device 30. See FIGS. 1 and 2. Additionally, the second configuration may be arranged so as to retain the access device within the recess 79 defined by the coupling surface 64 of the first portion and the coupling surface 74 of the second portion 72. For example, the attachable implement 60 may define a recess 79 that is smaller than the maximum outer dimension of the access device 30 so as to cause an interference fit between then attachable implement 60 and the access device 30. While the attachable implement 60 may compress and/or deform portions of the access device 30, it can do so at a level which does not substantially deform the internal lumen of the access device.

One or more of the resisting members 68 and 78 and/or the recess 79 can be arranged so as to provide a resistance to longitudinal movement of the attachable implement 60 along the access device 30. In some instances, the resistance provided by one or more of the resisting member 68 and 78 and/or the recess 79 is sufficient to resist forces normally experienced during use so as to prevent movement of the attachable implement 60 relative to the access device 30. For example, such resistance can be sufficient to require a force of greater than 2 Newtons applied to the attachable implement 60 in the direction of the longitudinal axis of the access device 30 in order to cause sliding movement of the attachable implement 60, more preferably in the range of about 3 Newtons to 10 Newtons, and most preferably about 4 to 5

Newtons. It will be understood that other force values could be utilized in varied circumstances depending for instance upon the particular percutaneously-introduced device and procedure requirements associated therewith. It will also be understood that the friction and resultant resistance to linear displacement of attachable implement 60 can depend, for instance, upon the extent of surface contact, the surface characteristics and materials of construction of the attachable implement 60 and those of the access device 30, which can also be varied in achieving the desired result. The variation of these and other parameters will be within the purview of those skilled in the field given the teachings herein.

In some instances, the present disclosure teaches attachable implements having multiple mechanisms for coupling the attachable implement to an access device. For example, the attachable implement 60 may slightly compress and/or deform the outer surface of the access device so as to cause an interference fit and/or increased frictional resistance to sliding movement of the attachable implement 60 along the surface of the access device 30. Additionally, the attachable implement 60 may comprise a one or more resisting members such as an adhesive and/or elastomeric rubber to further prevent movement of the attachable implement 60 along the body of the access device 30. These multiple coupling mechanisms provide increased resistance to movement of the attachable implement 60 along a portion of the access device 30 as well as a greater degree of reliability. Advantageously, the addition of a resisting member, such as an adhesive and/or elastomeric rubber, to a surface of the attachable implement 60 can increase the total resistance to movement of the attachable implement 60 without deforming an inner lumen of the access device. For example, the resisting member may increase the required force to cause sliding movement of the attachable implement 60 by at least 0.5 Newtons, such as from 2 Newtons to 2.5 Newtons. More preferably, the resisting member can increase the required force by at least 1 Newton. In some instances, the resisting member increases the required force by at least 0.5 to 5 Newtons.

In some instances, such as those illustrated in FIGS. 1-3, the portion of the access device 30 that is coupled to the attachable implement 60 extends in a direction transverse to a skin contacting surface of the attachable implement 60. For example, the portion of the access device 30 that is within the recess 63 and/or recess 79 can extend in a direction transverse to skin contacting surface 66 and/or skin contacting surface 76. This may be accomplished in a number of ways including, but not limited to, defining the recess 63 and/or the recess 79 in a direction that extends towards and/or away from the skin contacting surfaces 66 and/or 76 of the attachable implement 60. In some aspects, this arrangement allows for the skin contacting surfaces 66 and/or 76 of the attachable implement 60 to contact the skin of the patient at and/or near the insertion site so that little or no portion of the access device 30 is visible between the skin of the patient and the attachable implement 60. Advantageously, this improves the ability of a medical professional to identify when the access device 30 has migrated because any increase and/or decrease of visible section of the access device 30 extending between the attachable implement 60 and the insertion site in the skin of the patient will be more noticeable.

FIGS. 4-8 illustrate another embodiment of an attachable implement used for identifying the migration of a medical device. This embodiment comprises a attachable implement 90 having a first portion 92 and a second portion 96. Similar to the embodiments illustrated through the use of FIGS. 1-3, some embodiments of the attachable implement 90 illustrated in FIGS. 4-8 may be configurable between a first configuration and a second configuration. In some instances, the first configuration is an open-configuration (see FIGS. 5-7) arranged for sideably mounting of the attachable implement 90 onto an access device 30 and the second configuration is a closed-configuration (see FIGS. 4 and 8) arranged to couple the attachable implement 90 to the access device 30 and resist movement of the attachable implement 90 along a length of the access device 30.

Similar to some embodiments illustrated with the aid of FIGS. 1-3, some embodiments may be arranged so as to substantially surround the perimeter of an access device 30 and, in some instances, have one or more surfaces conforming to and/or matching the outer surface of the access device 30. Additionally, or alternatively, the attachable implement 90 may define a recess that is smaller than the maximum outer dimension of the access device 30 so as to cause an interference fit between then attachable implement 90 and the access device 30. Similar to the embodiments discussed above, one or more resisting members may be placed on surfaces of the attachable implement 90 that face the outer surface of the access device 30, such as the surfaces defining the recess for receiving the access device 30.

In some instances, the first portion 92 of the attachable implement 90 has an extension 94 arranged to be slidably positioned within a recess 98 of the second portion 96. When the attachable implement 90 is in an open configuration, the extension 94 extends between the first portion 92 and the second portion 96 of the attachable implement 90, allowing space for an access device 30 to be inserted into the recess formed by the first portion 92 and second portion 96. When the attachable implement 90 is in a closed configuration, the extension 94 is positioned within the recess 98 of the second portion 96, allowing the first portion 92 and the second portion 96 to be positioned adjacent to one another and substantially surround a portion of the access device 30.

Figure 8:
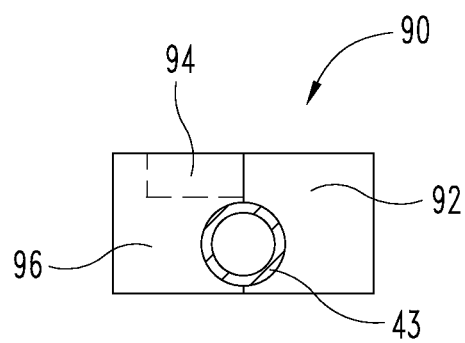
FIG. 8 is a front side view of the embodiment illustrated in FIG. 4 in a closed configuration.

FIG. 8 illustrates the attachable implement 90 having surfaces on the first portion 92 and the second portion 96 that substantially matching and/or adhering to the outer surface of the access device 30 when the attachable implement 90 is in a closed configuration. In some instances, it is preferred that the attachable implement 90 substantially surrounds the entire periphery of the access device 30. However, in some embodiments the attachable implement 90 surrounds only a portion of the periphery of the access device 30, such as sheath 43.

Figure 9:
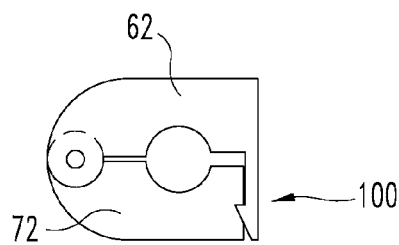
FIGS. 9 and 10 are front side views of one embodiment of the present disclosure.
Figure 10:
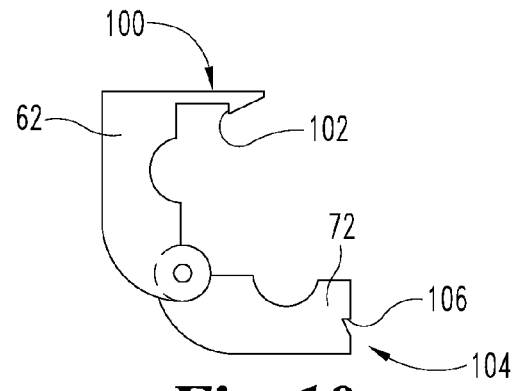

FIGS. 9-12 illustrate several embodiments capable of coupling the first portion to the second portion of the attachable implement body, such as the first portion 62 and the second portion 72 of the attachable implement 60 illustrated in FIGS. 1-3. As illustrated in FIGS. 9-10, a catch member 100 may extend from one or more portions of the attachable implement body. The portion opposite the one having the catch member 100 having a receiving area 104 arranged to receive the catch member 100 in coupling contact, so as to couple the portions of the attachable implement body to one another. For example, a locking surface 102 of a catch member 100 of the first portion may be arranged to mate with a locking surface 106 of a receiving area 104 of the second portion.

In some instances, the coupling member may be arranged for detachable coupling such that the first portion and second portion may be coupled to one another and then de-coupled from one another. For example, as illustrated in FIGS. 9-10, the catch member 100 may have a portion that is accessible to an operator after the first and second portions have been coupled to one another so that the operator may manipulate the catch member 100 and decouple locking surface 102 from locking surface 106.

Figure 11:
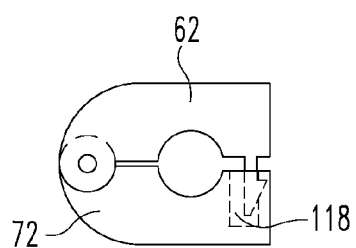
FIGS. 11 and 12 are front side views of one embodiment of the present disclosure.
Figure 12:
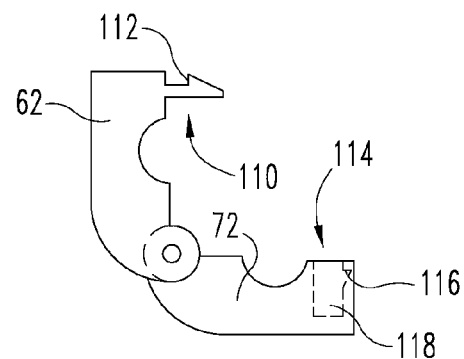

In other instances, the coupling member may be arranged such that it permanently couples the first portion and the second portion together. For example, as illustrated in FIGS. 11 and 12, a locking surface 112 of a catch member 110 of the first portion is arranged to mate with the locking surface 116 of a receiving area 114 of the second portion. When the attachable implement is in a closed configuration, the catch member 110 is received within the receiving area 114 of the second portion, and the locking surfaces 112 and 116 lock the first and second portions together. As will be appreciated, the catch member 110, when received within the receiving area 114, is contained within the periphery of the attachable implement body and is inaccessible to an operator of the attachable implement. This arrangement prevents the first and second portions of the attachable implement body from being decoupled accidentally and/or inadvertently.

Figure 13:
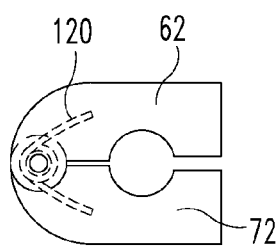
FIG. 13 is a front side view of one embodiment of the present disclosure.
Figure 14:
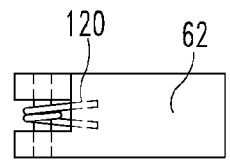
FIG. 14 is a top view of the embodiment illustrated in FIG. 13.

In some embodiments the attachable implement is arranged so as to be biased into an open configuration and/or a closed configuration. For example, as illustrated in FIGS. 13 and 14, a biasing member such as a spring 120 may be positioned on the attachable implement and cooperate with the first portion and/or the second portion so as to bias the first and second portions into an open or a closed configuration. However, as will be appreciated by one of ordinary skill in the art, other members besides springs may be used to bias the first and/or second portions into a first and/or second configuration, such as an open or closed configuration. For example, elastic materials, magnets and/or deflectable prongs may be used to deflect the first and second portions into a first and/or second configuration.

Figure 15:
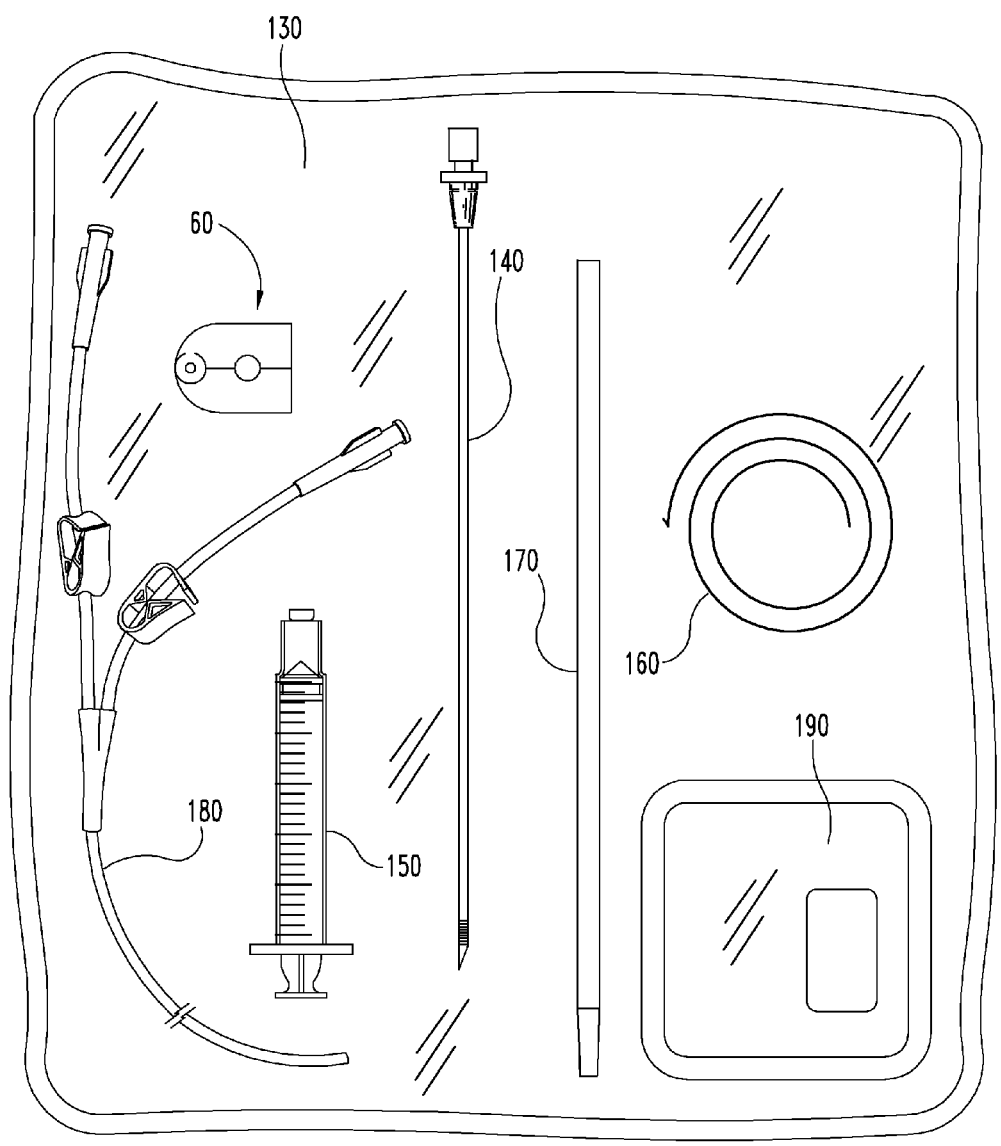
FIG. 15 illustrates one embodiment of a kit of the present disclosure.

FIG. 15 illustrates an embodiment of the present disclosure comprising a kit (not drawn to scale) containing the attachable implement for identifying the migration of a medical device. In some instances, the kit is sterilely packaged and contains the attachable implement along with other components used in a procedure involving a percutaneous access device 30. For example, as illustrated in FIG. 15, the attachable implement 60 may be included in a sterilely packaged container 130 with a needle 140, a syringe 150, a guidewire 160, a dilator 170, a catheter 180 and/or a catheter fixation device 190. In some embodiments, one ore more of the components contained within the kit are arranged to cooperate with one another. For example, the attachable implement 60 may have a coupling surface 64 and a coupling surface 74 that are arranged to mate with the outer surface with the catheter 180 when the attachable implement 60 is in a closed configuration. Additionally, or alternatively, in some instances the attachable implement 60 may be arranged so as to couple with the catheter fixation device 190 to fixedly couple the catheter 180 to a portion of the body of a patient, such as the skin, just to name one non-limiting examples.

The attachable implement 60 may be made of any material apparent to one of ordinary skill in the art to be suitable for the arrangements and uses described herein, such as metals and/or plastics. For example, the attachable implement 60 may comprise any suitable plastic material, such as polypropylenes, polybutylenes or polyamides, to name just a few non-limiting examples. In some instances, the attachable implement comprises biocompatible and/or hypo allergenic materials. Similarly, the attachable implement 60 may be formed by any suitable process, such as by injection molding, thermoforming, injection compression molding, or blow molding, to name just a few non-limiting examples.

Figure 16:
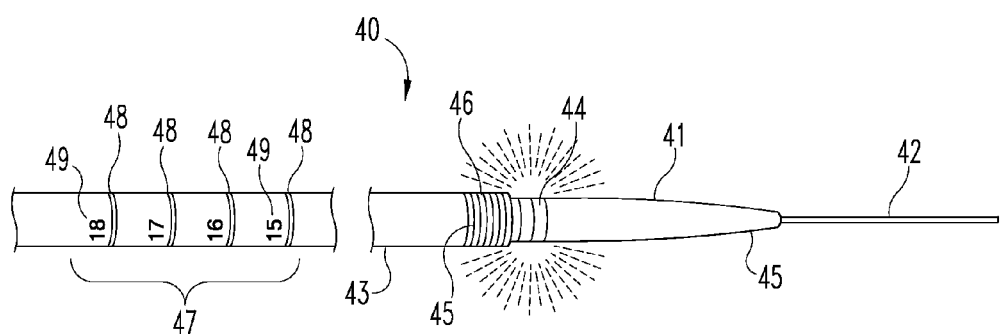
FIG. 16 is a partial cut-way perspective view of one embodiment of an IVUS-enabled device delivery system.

With reference to FIG. 16, shown is a partial cutaway view of a system useful for implanting a vascular device such as a filter. System 40 includes a dilator 41 for percutaneous introduction, a guide device 42 such as a wire guide, and an outer delivery sheath 43. Dilator 41 includes an IVUS probe 44 including one or more ultrasound transducers, such as piezoelectric crystal elements, for producing and/or receiving ultrasonic sound waves. IVUS probe 44 is preferably a rotating transducer, but a transducer array with a plurality of ultrasound transducers can also be provided as known. IVUS probe 44 and other IVUS elements disclosed herein can, for example, be configured to provide data for two-dimensional and/or three-dimensional IVUS images. IVUS probe 44 is connected electronically, such as by a wire and connector (not shown) positioned within or along dilator 41, to an IVUS imaging system that may include a display device and a computer processor for processing data gathered by IVUS probe 44 and displaying images correlated thereto. Sheath 43 of system 40 includes a distal tip region having an echogenic marker 45 and a fluoroscopic marker 46. Echogenic marker 45 and fluoroscopic marker 46 can be provided by the same physical structure or by differing physical structures.

In one embodiment, the markers 45/46 are both provided by a radiopaque material, such as platinum, titanium, tungsten or another metal (including alloys), positioned outside and/or within the material making up the body of the sheath 43. Illustratively, a platinum structure, such as a platinum hoop or ring, can be attached around the outside of sheath 43 to provide a fluoroscopically-discernible marker. Such a radiopaque structure can also contain structural features rendering it effective as an echogenic marker. These features may for example include dimples, grooves, or other textured surface features rendering the marker material visually discernible by ultrasound imaging. The fluoroscopic and/or echogenic markers can also be provided by other structures or materials or combinations thereof. Illustratively, in one embodiment, the markers 45 and 46 can be located closely adjacent one another, with the fluoroscopic marker 46 provided by a radiopaque material such as a metal, and the echogenic marker 45 provided by a separate element with any of the patterned features as discussed hereinabove for echogenic markers, or containing internal materials or features that have an acoustic impedance that significantly differs from the surrounding media so as to be discernible by ultrasonic imaging. The incorporated features or materials can include for example gas-filled spaces embedded within polymeric materials (e.g. bubbles), or acoustic impedance-mismatched, sonically-reflective materials such as glass, ceramic, metal or other particles (e.g. beads) incorporated within or coated upon a polymeric material. For additional information about echogenic markers that can be used herein, reference can be made for example to U.S. Pat. No. 5,201,314.

The markers 45/46 can be associated with sheath 43 in any suitable fashion including positioning on the outside, inside, within the body or wall of the sheath 43, or combinations thereof. Sheath 43 also includes a more proximally located marking feature 47 that is visible to the eye of the user when positioned externally of the patient. Visible marking feature 47 in the illustrated embodiment demarks the distance from locations within feature 47 to the distal tip of the sheath 43. For these purposes, the marking feature 47 can include a plurality of visible marking features 48 spaced longitudinally from one another along the length of sheath 43, such as lines, scores, or other markings partially or completely circumscribing the circumference of the sheath 43. In the illustrated embodiment, the marking feature 47 also includes numeric markings 49 associated with markings 48 which numerically indicate the distance of the respective associated markings 48 from the tip of the sheath 43. In one example, the marking feature 47 includes markings 48 offset longitudinally from one another by a regular distance such as 1 mm or 1 cm, and associated numerical markings 49 providing an indication of how many millimeters or centimeters, respectively, each marking 48 is spaced from the distal tip of the sheath 43. The marking feature 47 is positioned along the length of the sheath 43 such that at least some of or the entire marking feature 47 will occur externally of the patient during use of the sheath 43 to deliver the filter or other vascular device. For these purposes, the marking feature 47 can, for example, be positioned so as to include markings at skin level at a percutaneous insertion site through which system 40 is introduced. In this regard, it will be understood that other reference points external of the patient against which the marking feature 47 can be reliably tracked during a procedure to determine the distance to the distal tip of the sheath may also be used. Fixed external reference points are particularly useful for these purposes.

In one mode of use, the IVUS-enabled dilator 41 can be advanced within a vascular vessel of the patient along guide 42, and the IVUS probe 44 can be operated to generate signals translated to images of features of the vessel. IVUS probe 44 can then be positioned to and image a target position to which it is desired to move the distal tip of the sheath 43. Thereupon, the sheath 43 can be advanced coaxially along the dilator 41 until the distal tip of the sheath 43 detectably abuts or overlies IVUS probe 44 or regions proximate thereto. This detection can, for example, be by way of a tactile resistance to advancement of the sheath 43 over the IVUS probe 44 or some region or feature of sheath 43 proximate thereto, or by a change in an ultrasound image generated based signals from IVUS probe 44 due to the distal tip of the sheath 43 overlying some or all of IVUS probe 44 (for example, a change in the brightness of the image). This change in the image, in certain embodiments, can be enhanced by the presence of the echogenic marker 45 at the distal end region of sheath 43. At this point, the user knows that the distal tip of the sheath 43 is in essentially the same target position as the IVUS probe 44.

An external marker, such as any one of the attachable implements illustrated in FIGS. 1-14, may then be applied to the outer surface of the sheath 43 at a location proximal to the skin of the patient. Thereafter, the dilator 41 and guide 42 can be withdrawn from sheath 43, and a delivery catheter or other delivery instrument for delivering the vascular device can be advanced through sheath 43, while continuing to hold stable and/or monitor the position of the sheath 43 with its distal tip at the target position, such as maintaining position and/or contact of the external marker to the skin of the patient. In certain embodiments, the distal tip of the vascular implant to be deployed can then be aligned with the distal tip of the sheath 43 while maintaining the stable position of the sheath 43, and sheath 43 can be withdrawn proximally a distance while holding stable the position of the delivery instrument to reliably deploy the vascular device at the target site. In some instances, the external marker remains in position on the outer surface of the sheath during the procedure (e.g., deployment of the vascular device).

The alignment of the distal end of the vascular implant with the distal end of the sheath 43 can be accomplished in any suitable manner, including by tracking the position of the distal tip of the vascular implant ultrasonically (e.g. transabdominally with the assistance of a tip-located echogenic markers, such as a marker on a vena cava filter and marker 45 on sheath 43) and/or through other means. In certain embodiments, the vascular device is carried by a delivery catheter or other instrument having a first visible marker that remains external of the patient and which aligns with an external reference point, such as the proximal end of the sheath 43 or a connected accessory (e.g. a Touhy-Borst adaptor), when the distal end of the vascular implant is at the distal tip of the sheath 43. The delivery instrument may also include a second visible marker, proximal to the first visible marker, to which the sheath can be withdrawn, to signal a stage of deployment, e.g. when the vascular implant has been completely deployed out of the sheath. Other measures for accomplishing similar signaling alignments may also be used.

Figure 17:
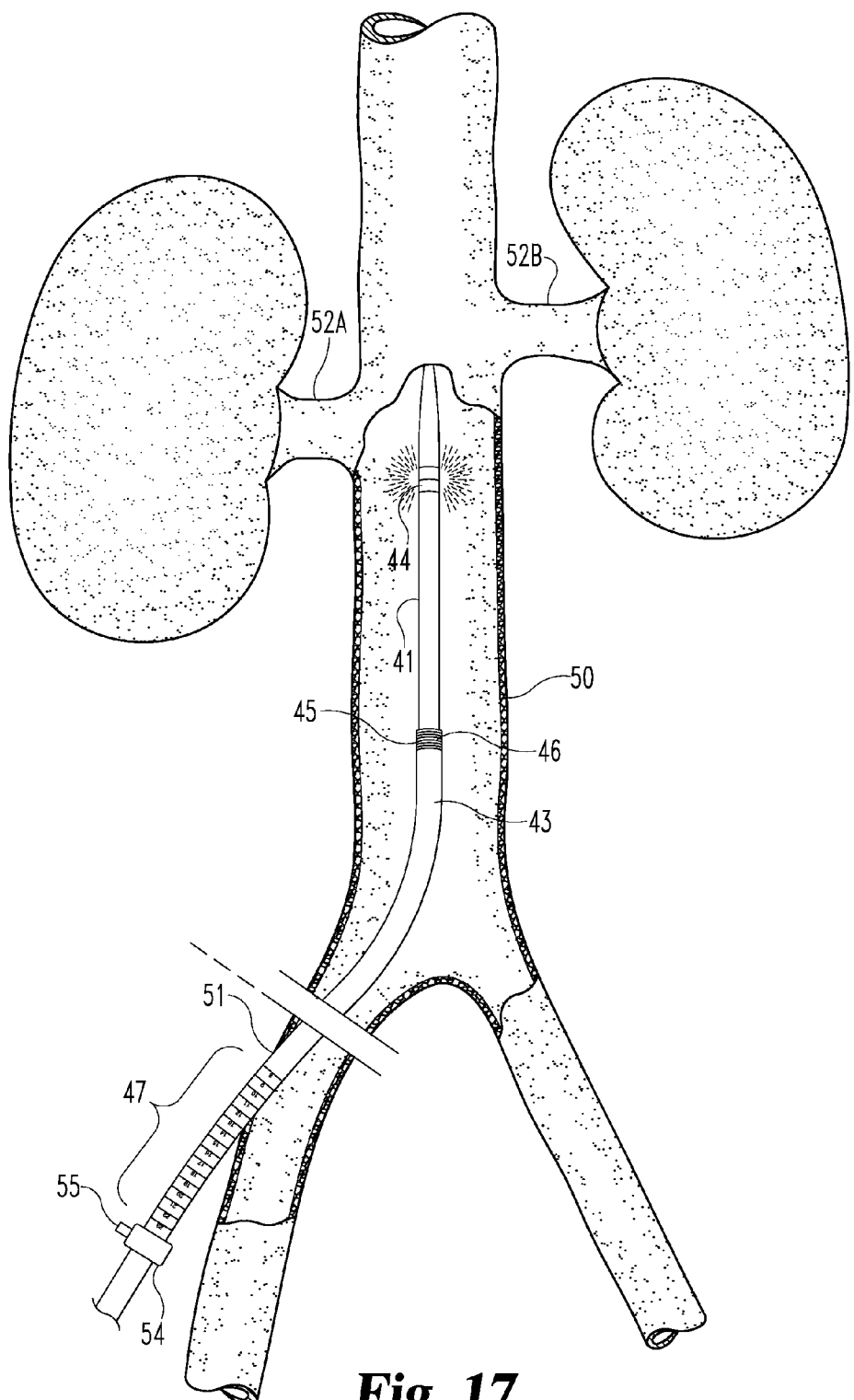
FIGS. 17, 18, 19, 20, and 21 illustrate devices and steps used in certain embodiments for the delivery of a filter device.
Figure 18:
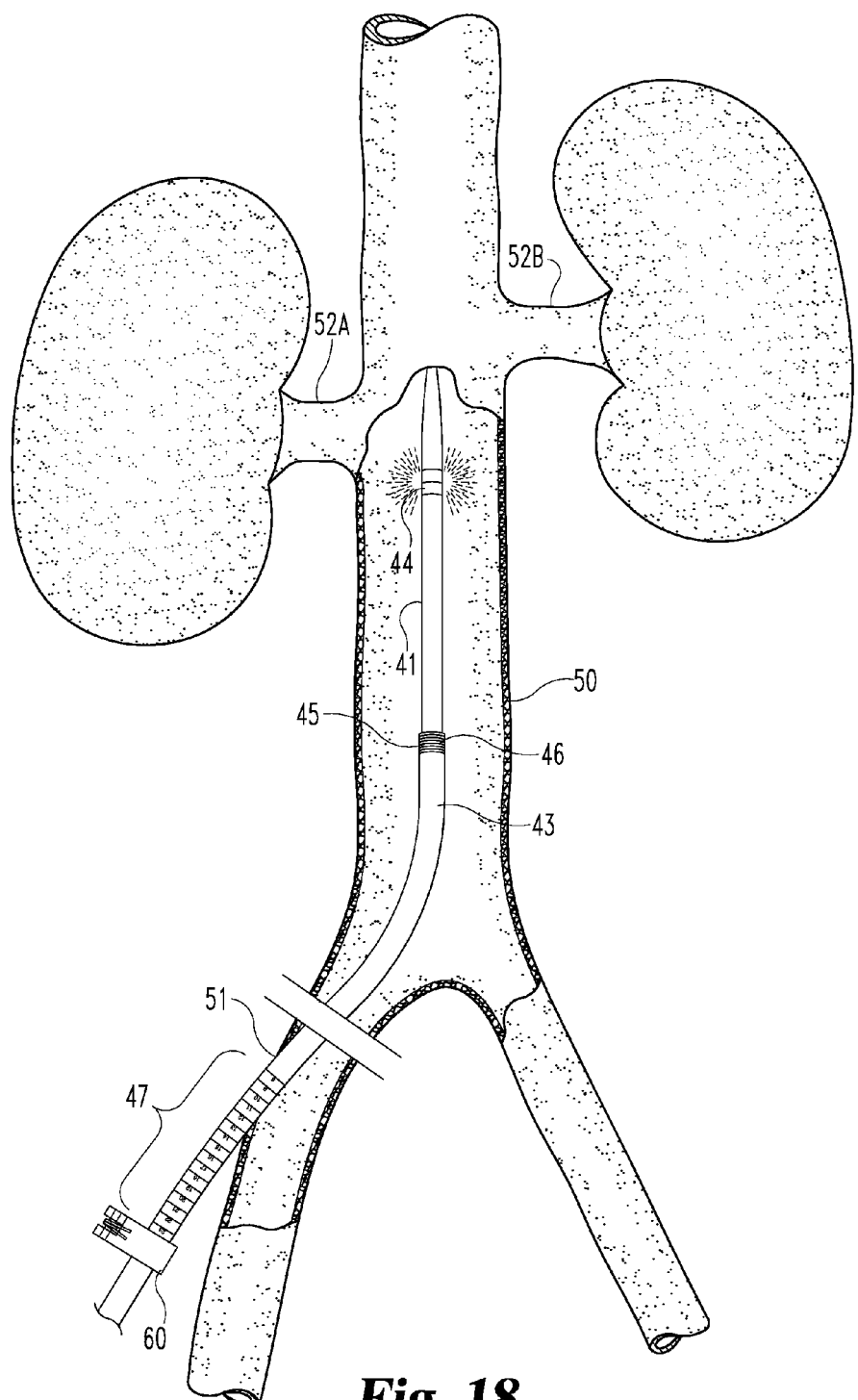
Figure 19:
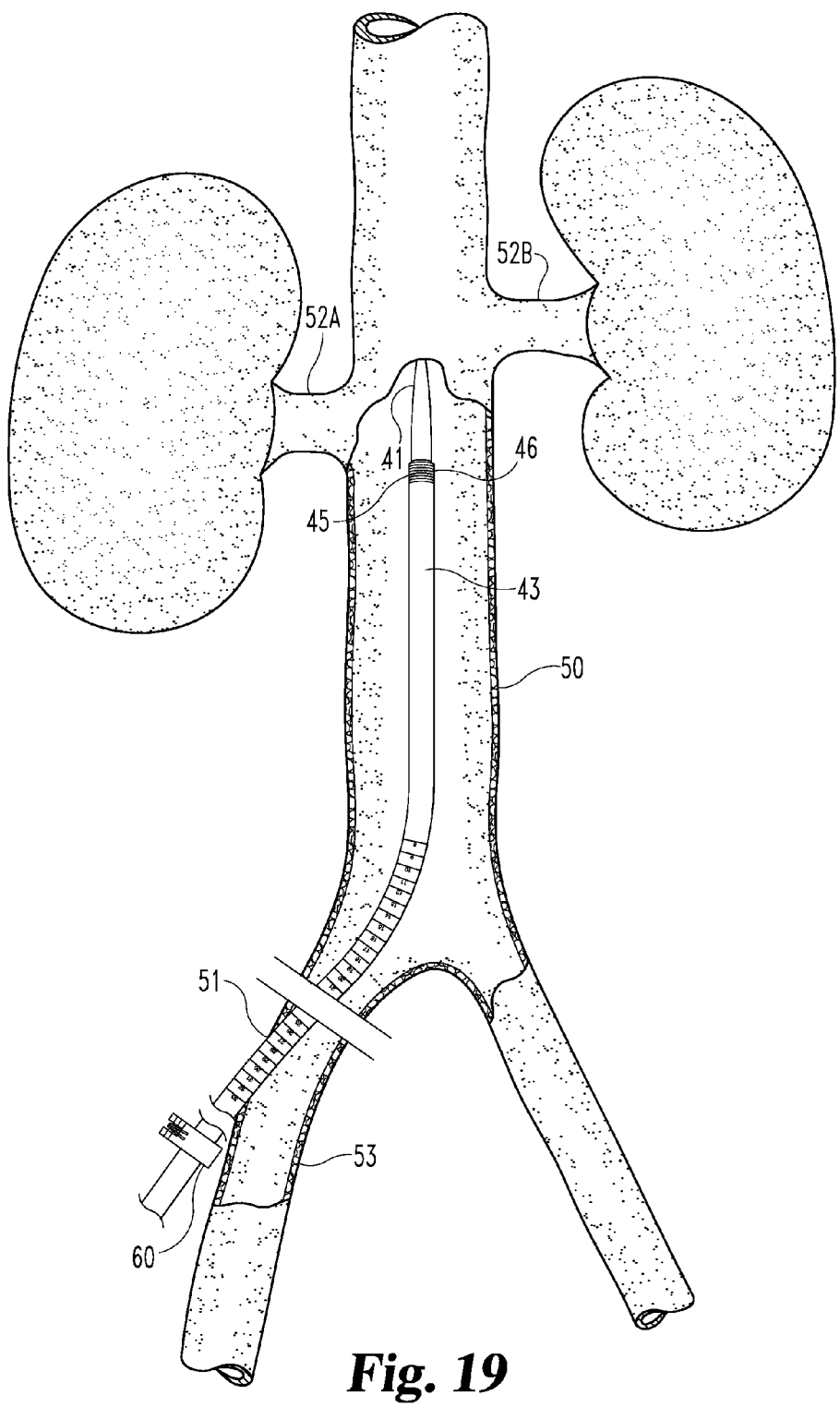
Figure 20:
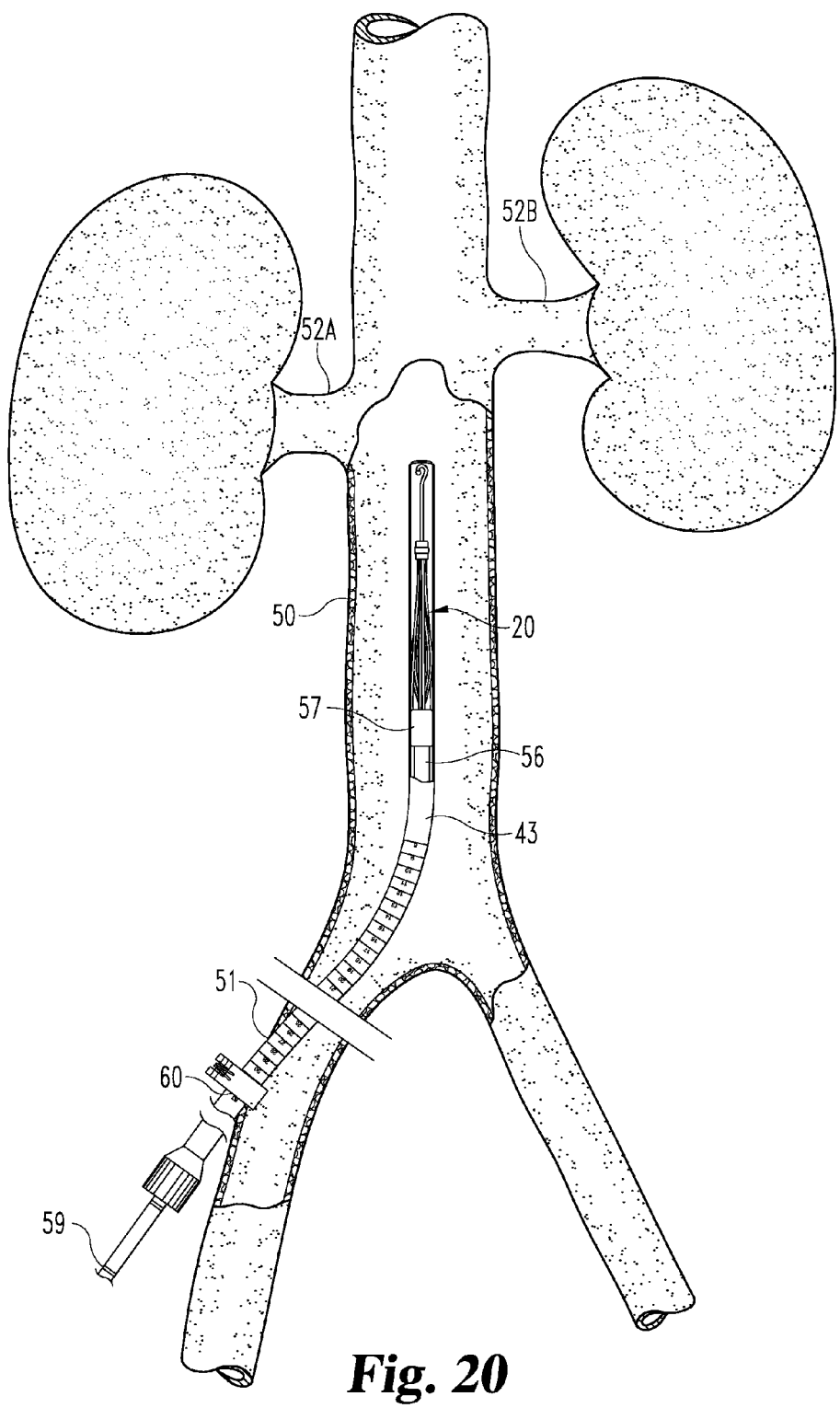
Figure 21:
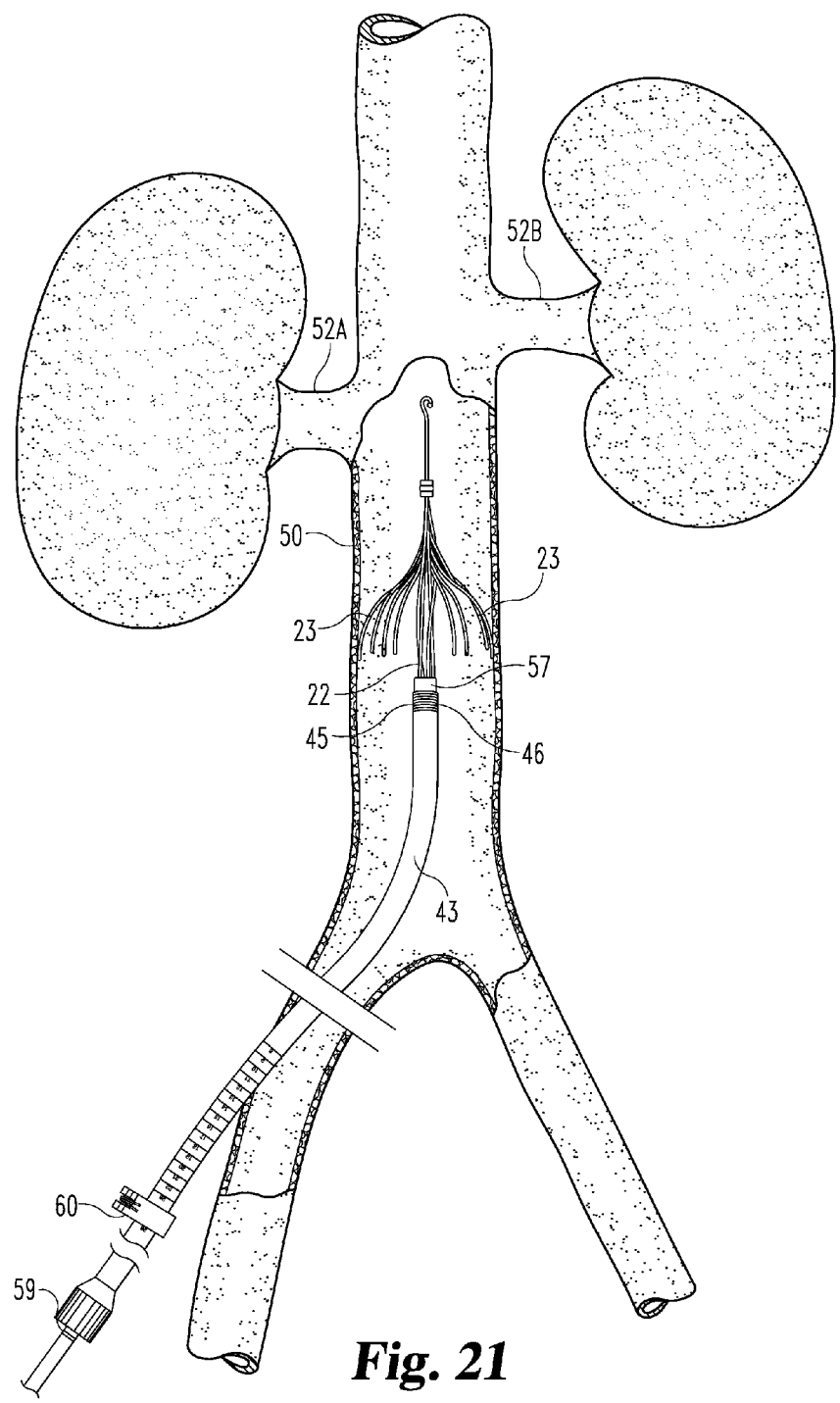

The use of system 40 of FIG. 16 to deliver a vena cava filter to a patient will now be described with reference to FIGS. 17-21. FIG. 17 shows system 40 having been introduced into the vena cava 50 through a percutaneous access site 51 in the right femoral vein of a patient. Right renal vein 52A and left renal vein 52B feed into the vena cava 50, and in the illustrated embodiment it is desired to deploy a filter generally below the renal veins 52A and 52B, or "caudal" thereto. Depicted in FIG. 17 is dilator 41 advanced into vena cava 50 and at a position at which IVUS probe 44 can generate an image of at least the lowest-positioned renal vein, in most instances that being the right renal vein 52A. Prior to reaching this position, the IVUS probe 44 can be used to generate images of vascular landmarks distal to the renal veins, for example the right atrium, the hepatic veins, or other features. In certain embodiments the IVUS probe 44 will have a longitudinal resolution such that an image showing both renal veins 52A and 52B can be obtained. Sheath 43 is also percutaneously inserted into the vena cava, which insertion may have been before, with, or after that of dilator 41. The distal tip of sheath 43 is shown positioned well below the IVUS probe 44 so that it does not obscure IVUS probe 44 and thereby degrade generated image data. As can also be seen, the marking feature 47 includes at least portions remaining at skin level on the patient, and demarking the shaft distance from skin level to the distal tip of sheath 43.

Further, in the illustrated embodiment, a repositionable scale marker 54 is positioned about sheath 43 and can be advanced to locations within marker feature 47. Scale marker 54 can include a stop or locking mechanism 55 which can be actuated to selectively release and secure the position of scale marker 54 along sheath 43. Any suitable mechanism can be used for this purpose including, for example, spring actuated friction stops against the sheath 43, tightenable screws or knobs which abut sheath 43 or cinch marker 54, or the like.

As illustrated in FIGS. 18-21, an attachable implement such as those shown and explained in conjunction with FIGS. 1-14 can be used to determine whether an access device, such as a sheath 43, has migrated. For example, after the IVUS probe 44 is located in the desired position, while holding the position of IVUS probe 44 stationary, sheath 43 is advanced coaxially over dilator 41 until the distal tip of sheath 43 advances over IVUS probe 44. This event can be sensed tactilely as discussed above, and/or through a change in the image generated by IVUS probe 44 due to being covered by the wall of sheath 43 (potentially enhanced by the presence of echogenic marker 46, which can be configured to reflect ultrasonic energy sourced from the probe 44 within). At this point, the user knows that the distal tip of sheath 43 is positioned at the target position found with the IVUS probe 44. The user can then reference the scale markings within the marking feature 47 that coincide with the skin level of the percutaneous insertion site 51. A correlation can thereby be drawn between the positioning of the distal tip of the sheath 43 at the target site and a scale marking within marking feature 47. Again, in one embodiment, such scale marking includes a numeric value correlating to the distance from the marking to the distal tip of sheath 43.

The marking attachable implement 60 is coupled to the outer surface of the sheath 43 at a position adjacent to and/or abutting the surface of the skin around the percutaneous insertion site 51 with the distal tip of sheath 43 at this target position. For example, the coupling surface 64 of the first portion 62 and the coupling portion 74 of the second portion 72 can be fixedly coupled to the outer surface of the sheath 43. The dilator 41 and, if still present, the wire guide can then be removed from the sheath 43 while holding the sheath 43 stably in position with the marking attachable implement 60 adjacent to and/or abutting the surface of the skin around the percutaneous insertion site 51. When the marking attachable implement 60 is in the same position as it was when first attached to the sheath 43, the operator is assured that the distal tip of sheath 43 is at and/or near its target position.

A delivery catheter or other delivery instrument for delivering the vascular device can be advanced through sheath 43, while continuing to hold stable the position of the marking attachable implement 60 relative to the body of the patient (e.g., the surface of the patient's skin around the percutaneous insertion site 51). In certain embodiments, the distal tip of the vascular implant to be deployed is then aligned with the distal tip of the sheath 43 while the position of the marking attachable implement 60 is maintained adjacent to and/or abutting the skin. When the vascular implant is in its desired deployment position, the sheath 43 is withdrawn proximally a distance while the delivery instrument is held stable in position, so as to reliably deploy the vascular device at the target site. For example, sheath 43 can be withdrawn until the proximal end of sheath 43 (or the associated reference point) is flush with marker 59, whereupon filter 20 is externalized from sheath 43 at the target location. After release of primary struts 22 from retaining element 57, filter 20 fully deploys in vena cava 50, and sheath 43 and any other percutaneously introduced devices can thereafter be withdrawn from the patient.

If at any point during the withdrawal of the dilator 41, the wire guide, and/or the insertion of the delivery catheter or other delivery instrument the marking attachable implement 60 moves from its position relative to the skin, the operator can observe that the distal tip of the sheath 43 has moved from its target position. For example, if the operator observes that the reference marker 60 is closer or further away from the skin of the patient than when the attachable implement 60 was first attached (at the time the distal tip of the sheath 43 was in the target position), then the operator will know that the distal tip of the sheath 43 has moved from the target position. Similarly, if the attachable implement 60 was coupled to the sheath 43 at a point near the skin of a patient when the distal tip of the sheath 43 was in the target position, then any observation that the marking attachable implement 60 is being pressed into the surface of the skin, such as depressed area of tissue around the percutaneous insertion site 51, is an indication that the distal tip of the sheath 43 is past the target location.

Another benefit of the attachable implements illustrated and described above is that they provide a stop that resists the movement of the access device, such as sheath 43, in at least one direction. In particular, several attachable implements disclosed resist movement of the access device along a direction into the body of the patient. For example, skin contacting surface 66 of the first portion 62 of attachable implement 60 resists the further insertion of the sheath 43 into the body of the patient, when the attachable implement 60 is coupled to the sheath 43. In some instances, the attachable implement, such as attachable implement 60, is arranged to resist movement in multiple directions. For example, the attachable implement may have a portion that is detachably coupled to a securement device affixed to the skin of the patient.

In advantageous operations, after deployment of the filter 20 from sheath 43 and release of the primary struts 22 from retaining device 57, the filter introducer 56 is withdrawn while leaving sheath 43 percutaneously inserted. The guide 42 can then be reinserted through sheath 43 and an IVUS-enabled catheter such as dilator 41 can be reintroduced over the guide 42. With the guide 42 extending into or beyond the filter 20, the IVUS-enabled dilator 41 can be advanced within vena cava 50 and the IVUS probe 44 can be used in the generation of images to confirm the deployment position of filter 20. In one mode, the IVUS images generated can be used to inspect the position of the primary struts 22 and/or secondary struts 23 against the wall of vena cava 50. To facilitate this inspection, echogenic markers are positioned on struts 22 and/or 23 and configured to be apposed against the wall of vena cava 50 upon proper deployment of the filter 20 can be used to generate images from which such apposition can be confirmed or denied. The IVUS probe 44 can also if desired be advanced beyond filter 20 to generate an image of renal vein or veins 52A and/or 52B to confirm position of the filter 20 caudal thereto. After this inspection, and potentially also electronic storage of the confirming images for the patient record, the guide device 42 and IVUS-enabled dilator 41 can be withdrawn from the patient.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Of course, variations of those preferred embodiments will become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. In addition, all publications cited herein are indicative of the abilities of those of ordinary skill in the art and are hereby incorporated by reference in their entirety as if individually incorporated by reference and fully set forth.

The invention claimed is:

1. An attachable implement for identifying migration of an elongate medical device that extends through the skin of a patient, comprising:
    an attachable implement body comprising a first coupling surface and a first skin contacting surface on a first portion and a second coupling surface and a second skin contacting surface on a second portion;
    said first and second portions configurable from an open configuration to a closed configuration; and
    a biasing member arranged to bias the first and second portions from the open configuration into the closed configuration;
    wherein said first and second coupling surfaces are arranged to couple to an outer surface of the elongate medical device;
    wherein said first and second skin contacting surfaces are arranged to contact the skin of the patient;
    wherein in said open configuration said attachable implement body is arranged to be mountable onto the elongate medical device from a direction transverse to a longitudinal axis of the elongate medical device and receive the elongate medical device between the first and second portions;
    wherein when said attachable implement body is mounted onto the elongate medical device the elongate medical device extends in a direction transverse to said first and second skin contacting surfaces; and
    wherein when in said closed configuration around the elongate medical device, said attachable implement body is configured to move with the elongate medical device from a first position where the first and second skin contacting surfaces are adjacent to the patient's skin to a second position where the first and second skin contacting surfaces are remote from the patient's skin, such that an operator may identify that the elongate medical device has migrated.

2. The attachable implement of claim 1, wherein:
    said first and second portions are pivotably coupled to one another.

3. The attachable implement of claim 1, wherein:
    said first and second portions are slidably coupled to one another.

4. The attachable implement of claim 1, further comprising:
    a recess defined by said first and second portions and arranged to receive a portion of the elongate medical device.

5. A kit, comprising:
    a sheath;
    an inner catheter; and
    an attachable implement for identifying migration of said sheath when said sheath extends through the skin of a patient;
    the attachable implement including an attachable implement body having a first coupling surface and a first skin contacting surface on a first portion and a second coupling surface and a second skin contacting surface on a second portion, the first and second coupling surfaces having an adherent material positioned thereon;
    said first and second portions configurable from an open configuration to a closed configuration wherein the first and second coupling surfaces face one another;
    said first and second coupling surfaces arranged to mate with an outer surface of said sheath;
    said first and second skin contacting surfaces arranged to contact the skin of the patient; and
    said adherent material positioned on said first and second coupling surfaces arranged to adhere said first and second coupling surfaces to the outer surface of said sheath;
    wherein said attachable implement body is configured to move with said sheath from a first position where the first and second skin contacting surfaces are adjacent to the patient's skin to a second position where the first and second skin contacting surfaces are remote from the patient's skin, such that an operator may identify that said sheath has migrated;
    wherein said attachable implement body requires a force of greater than 2 Newtons when in said closed configuration around said sheath to slide said attachable implement along a length of said sheath; and
    wherein said inner catheter is slidably receivable within said sheath when said attachable implement is in said closed configuration around said sheath.

6. The it claim 5, further comprising:
    a removable film positioned over said adherent material and arranged to protect said adherent material prior to adherence to said sheath.

7. The kit of claim 5, wherein:
    said first and second portions are pivotably coupled to one another.

8. The kit of claim 5, wherein:
    said first and second portions are slidably coupled to one another.

9. The kit of claim 5, further comprising:
    a recess defined by said first and second portions and arranged to receive a portion of said sheath.

10. The kit of claim 5, further comprising:
    a biasing member arranged to bias the first and second portions from said open configuration into said closed configuration or from said closed configuration into said open configuration.

11. The kit of claim 10, wherein:
    said biasing member biases said first and second portions from said open configuration into said closed configuration.

12. An attachable implement for identifying migration of a medical device that extends through the skin of a patient, comprising:
    an attachable implement body comprising a coupling surface, an adherent material, and a skin contacting surface;
    the attachable implement configurable from an open configuration to a closed configuration;
    a biasing member arranged to bias the attachable implement from the open configuration into the closed configuration;
    said coupling surface arranged to mate with a surface of the medical device;
    said skin contacting surface arranged to contact the skin of the patient; and said adherent material positioned on said coupling surface and arranged to adhere said coupling surface to the surface of the medical device;

wherein said attachable implement body is arranged to be mountable onto the medical device from a direction transverse to a longitudinal axis of the medical device; and wherein said attachable implement body is configured to move with the medical device from a first position where the skin contacting surface is adjacent to the patient's skin to a second position where the skin contacting surface is remote from the patient's skin, such that an operator may identify that the medical device has migrated.

13. The attachable implement of claim 12, further comprising:

a removable film positioned over said adherent material and arranged to protect said adherent material prior to attachment to the medical device.

14. A method for detecting movement of a heath implanted through the skin of a patient using the attachable implement of claim 1, comprising:

coupling the attachable implement to the sheath at a location proximal to the skin of the patient;

advancing a vascular device through the sheath; and monitoring the attachable implement for movement before and after advancing the vascular device through the sheath so as to detect movement of the medical device.

15. The attachable implement of claim 1, comprising:

a catch member extending from said first portion and arranged to couple said first portion to said second portion when said first and second portions are in said closed configuration.

16. The kit of claim 5, wherein:

said attachable implement includes a catch member extending from said first portion and arranged to couple said first portion to said second portion when said first and second portions are in said closed configuration.

17. The attachable implement of claim 12, comprising:

a catch member extending from a first portion of said attachable implement and arranged to couple said first portion to a second portion of said attachable implement when said attachable implement is in said closed configuration.

* * * * *

UNITED STATES PATENT AND TRADEMARK OFFICE
CERTIFICATE OF CORRECTION

PATENT NO. : 9,492,638 B2  
APPLICATION NO. : 14/068737  
DATED : November 15, 2016  
INVENTOR(S) : McKinnis et al.

It is certified that error appears in the above-identified patent and that said Letters Patent is hereby corrected as shown below:

In the Claims

In Column 16, Line 30 (approx.), Claim 6, change the phrase "The it claim 5" to "The kit of claim 5".

In Column 17, Line 20 (approx.), Claim 14, change the word "heath" to "sheath".

Signed and Sealed this  
Eleventh Day of April, 2017

Michelle K. Lee  
*Director of the United States Patent and Trademark Office*